United States Patent
Price et al.

(10) Patent No.: US 12,078,628 B2
(45) Date of Patent: Sep. 3, 2024

(54) IN VITRO RELEASE TESTING (IVRT) DEVICE FOR ORALLY INHALED DRUG PRODUCTS

(71) Applicant: NANOPHARM LIMITED, Newport (GB)

(72) Inventors: Robert Price, Chepstow (GB); Arron Danson, Ross-on-Wye (GB); Gregor Strniša, Radeče (SI)

(73) Assignee: NANOPHARM LIMITED, Newport (GB)

( * ) Notice: Subject to any disclaimer, the term of this patent is extended or adjusted under 35 U.S.C. 154(b) by 297 days.

(21) Appl. No.: 17/776,670

(22) PCT Filed: Nov. 15, 2019

(86) PCT No.: PCT/EP2019/081551
§ 371 (c)(1),
(2) Date: May 13, 2022

(87) PCT Pub. No.: WO2021/093979
PCT Pub. Date: May 20, 2021

(65) Prior Publication Data
US 2022/0404326 A1    Dec. 22, 2022

(51) Int. Cl.
*G01N 33/15*    (2006.01)
*B01D 63/08*    (2006.01)
*B01D 69/10*    (2006.01)

(52) U.S. Cl.
CPC .......... *G01N 33/15* (2013.01); *B01D 63/087* (2013.01); *B01D 69/10* (2013.01); *B01D 2313/025* (2013.01); *B01D 2325/0283* (2022.08)

(58) Field of Classification Search
CPC .......... B01D 2313/02; B01D 2313/025; B01D 2265/00–06; B01D 63/087; B01D 69/10;
(Continued)

(56) References Cited

U.S. PATENT DOCUMENTS

| | | | |
|---|---|---|---|
| 6,929,782 B1 * | 8/2005 | Ciliberto | G01N 13/00 422/561 |
| 7,934,434 B2 * | 5/2011 | Shelton | G01N 1/2205 73/864.34 |
| 10,724,928 B2 * | 7/2020 | Price | G01N 15/0272 |

FOREIGN PATENT DOCUMENTS

| WO | 00/46597 A1 | 8/2000 |
|---|---|---|
| WO | 2017/051180 A1 | 3/2017 |

OTHER PUBLICATIONS

Ben Forbes et al., "In Vitro Testing for Orally Inhaled Products: Developments in Science-Based Regulatory Approaches", The AAPS Journal, 2015, pp. 837-852, vol. 17, No. 4.
(Continued)

*Primary Examiner* — Justin N Olamit
(74) *Attorney, Agent, or Firm* — Sughrue Mion, PLLC

(57) ABSTRACT

An in vitro release testing (IVRT) device for orally inhaled drug products, for use in an IVRT apparatus, the device having an air-permeable filter loaded with particulate material representing a dose of an orally inhaled drug product. The device has an upper filter support element and a lower filter support element, the loaded filter being circumferentially retained between the upper and lower support elements, a filter cover to cover the upper surface of the loaded filter, and a filter cover retainer provided to assemble and seal the IVRT device.

16 Claims, 6 Drawing Sheets

(58) Field of Classification Search
CPC ........... B01D 2325/0283; G01N 33/15; G01N 1/2205; G01N 1/2223
See application file for complete search history.

(56) References Cited

OTHER PUBLICATIONS

International Search Report of PCT/EP2019/081551 dated Aug. 25, 2020 [PCT/ISA/210].
Written Opinion of PCT/EP2019/081551 dated Aug. 25, 2020 [PCT/ISA/237].
International Preliminary Report on Patentability of PCT/EP2019/081551 dated Oct. 11, 2021 [PCT/IPEA/409].

\* cited by examiner

IN VITRO RELEASE TESTING (IVRT) DEVICE FOR ORALLY INHALED DRUG PRODUCTS

CROSS REFERENCE TO RELATED APPLICATIONS

This application is a National Stage of International Application No. PCT/EP2019/081551 filed on Nov. 15, 2019.

The invention concerns an in vitro release testing (IVRT) device for orally inhaled drug products.

In vitro release testing (IVRT) has been commonly used to measure the release and diffusion of locally-acting, semi-solid dosage forms for topical based products. A release profile enables the determination of the in vitro release rate (IVRR), a kinetic parameter which can provide critical quality attributes on the physical and chemical properties of the active pharmaceutical ingredient and the microstructural characteristics of the formulated product. While IVRT is well established in the research community and shares the same basic principles as compendial dissolution methods for orally administered formulations, it is only recently that regulatory agencies have begun to address the application and validation of IVRT as an alternative bioequivalence assessment tool for locally acting topical drug products. In 2016, the U.S. Food and Drug Administration (FDA) drafted a guidance on the development and a validation methodology of IVRT testing for a 5% acyclovir cream.

These IVRT pivotal tests need to be performed in a manner compatible with the general procedures and statistical analysis method specified in the United States Pharmacopeia (USP) General Chapter <1724>: Semisolid Drug Product-Performance Tests. These include different models of a vertical diffusion cell (VDC), an immersion cell, and a flow through cell used with a USP Apparatus 4. These systems are shown in FIGS. 1 to 3.

The most common IVRT technique is the vertical diffusion cell (VDC) system, or more commonly known as the Franz cell, shown in FIG. 1, which consists of two chambers (a donor chamber and a receptor chamber) separated by a membrane that acts as a physical barrier for diffusion. The ideal membrane needs to have minimal resistance to mass transport of the drug, no drug binding and minimal thickness. The VDC chambers are held together by a clamp, screw top or other means. For most semisolid dosage testing, a defined amount of the sample sits on a synthetic, inert membrane contained within a sample chamber cavity that is occluded with a glass supporting disk. The receptor media is maintained at constant temperature and held under sink conditions for the duration of the test.

The in vitro release rate can also be determined using an immersion cell type apparatus, shown in FIG. 2. This system is based on the USP Paddle-over disk Apparatus V method for testing transdermal patches, where a Teflon cell is placed at the bottom of a dissolution vessel. The cell keeps the dosage form and the receptor medium separated from the receptor media via a synthetic membrane.

The third method is based on a USP 4 flow-through cell apparatus, shown in FIG. 3, where the sample is contained within a small insertion cell, which contains a reservoir and a ring to hold the synthetic membrane. The reservoir is available in different sizes to accommodate different volumes of the semisolid product. The cell is inserted into a USP 4 flow-through cell with the membrane facing downward and the prepared cell inserted in a heating jacket. The release reservoir volume needs to be adapted to achieve sink conditions and ensure precision of the analytical method.

The general principles of these techniques are quite similar, requiring the separation of a drug receptor and a receptor chamber by a mounted synthetic membrane, with an exposed orifice of known diffusional area for drug release.

One goal of the present invention is to adapt the above systems to receive a representative aerosol dose for release testing of any orally inhaled drug product.

The present invention also aims to provide an IVRT apparatus that is simple and cheap to manufacture and to assemble, an easy to use in a reliable manner.

The present invention thus provides an in vitro release testing (IVRT) device for orally inhaled drug products, for use in an IVRT apparatus, said device comprising an air-permeable filter loaded with particulate material representing a dose of an orally inhaled drug product, said device comprising:
- an upper filter support element and a lower filter support element, said loaded filter being circumferentially retained between said upper and lower support elements,
- a filter cover to cover the upper surface of said loaded filter (F), and
- a filter cover retainer provided to assemble and seal the IVRT device.

Advantageously, the device further comprises a holder member receiving the lower filter support element and cooperating with said filter cover retainer for the sealed assembly of the IVRT device.

Advantageously, a mesh is provided between said lower filter support element and said loaded filter to cover the lower surface of said loaded filter.

Advantageously, said filter cover retainer comprises legs providing a bayonet-type fitting on said holder member.

Advantageously, said filter cover retainer cooperates directly with said lower filter support element for the sealed assembly of the IVRT device.

Advantageously, said filter is selected from woven fabrics, nonwoven fabrics, meshes and air-permeable films.

Advantageously, the filter comprises a fabric formed from glass microfibers, synthetic cellulose based materials, or from filaments of a polymeric material selected from polycarbonate, polyester, polyolefins, polyamides, polyvinylchlorides and polyetheretherketones.

Advantageously, the filter comprises a metal mesh, for example a stainless steel mesh.

Advantageously, said filter has a pore size of not more than 5 µm, preferably not more than 3 µm.

Advantageously, said filter has a pore size of at least 1 µm.

Advantageously, said filter has an air permeability which is such that the filter generates a reduction in flow rate of not more than 20%, preferably not more than 15%, more preferably not more than 10% relative to absence of a filter.

Certain embodiments of the invention will be described below with reference to the accompanying drawings, given as non-limiting examples, in which.

The present invention makes use of an apparatus for collection of particles of an inhalable formulation. Document WO2017051180A1, which is incorporated here as a reference, discloses such an apparatus.

The apparatus of WO2017051180A1 includes a dose collection section, which includes a filter F. The filter F is arranged orthogonally with respect to the direction of flow of the pneumatic flow downstream of the orifice. Advantageously, at the point of impact with the filter, the conditions are of relatively uniform and low-velocity pneumatic flow.

Figure 4:
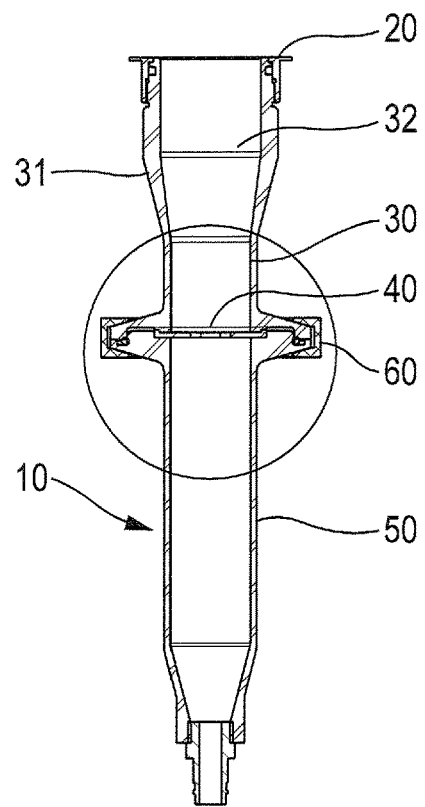
FIG. 4 is a sectional view of a dose collection device according to an advantageous embodiment.
Figure 5:
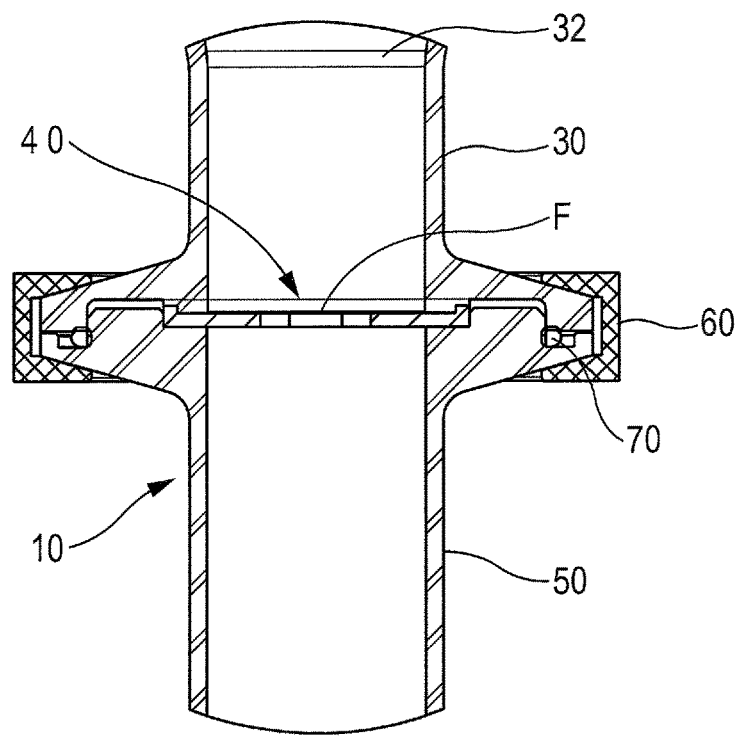
FIG. 5 is an enlarged view of detail D1 of FIG. 4.

One advantageous embodiment of a dose collection section 10 is shown in FIGS. 4 and 5.

The dose collection device 10 of FIG. 4 comprises, taken from the top to the bottom of FIG. 4, an upper adapter element 20, an upper body 30, a filter unit 40, a lower body 50 and a clamping device 60, used to clamp upper and lower bodies together.

Upper body 30 comprises a funnel 31 that defines an inlet orifice 32. The funnel 31 is tapered to reduce the occurrence of sharp edges, which may induce turbulence, and is arranged to deliver the fluid flow into an unimpeded vertical pathway extending downwardly from orifice 32 towards the filter unit 40.

The filter F is supported by the filter unit 40 that will be described in more detail hereafter.

The area of orifice 32 is similar to, but slightly less than, the exposed area of filter F on which deposit occurs.

A suction source, not shown in the drawings, is in pneumatic communication with the filter F on the side remote from the orifice 32 and serves to draw air through the pathway including the orifice 32, and filter F in the downward direction in FIGS. 4 and 5.

A flow controller (not shown) can be associated with the suction source for maintaining suitable flow conditions.

The lower body 50 receives the filter unit 40 on its top surface. As seen on FIG. 15, said top surface comprises an O-ring 70, which provides the principle air path seal of the apparatus upon clamping. The top surface also comprises first recesses 51, to provide rotational alignment of the filter unit 40 on the lower body 50. Second recesses 52 are provided to allow manual, semi-automatic or automatic extraction of the filter unit 40 from the lower body 50 upon releasing the clamping device 60.

The filter F can be any filter that is appropriate for retaining particles in the range of up to 5 µm, for example in the range of from 0.5 µm to 5 µm. For example, there may be used filters with pore size of up to 3 µm.

Advantageously, the filter has an air permeability which is such that the filter generates a reduction in flow rate of not more than 20%, preferably not more than 15%, more preferably not more than 10% as compared with the flow rate in absence of a filter. Such filters may, but do not necessarily, have a pore size of at least 1 µm.

The filter may, for example, be selected from woven fabrics, nonwoven fabrics, meshes and air-permeable films. In some embodiments, the filter comprises a fabric formed from glass microfibers or from filaments of a polymeric material selected from polycarbonates, polyesters, polyolefins, polyamides (for example nylons), acrylics, acrylic copolymers, polyvinylchlorides and polyetheretherketones. Suitable polyolefins include, for example, polyethylene, polypropylene and ethylene and propylene copolymers with one or more other monomers. The filter can also comprise synthetic cellulose based materials, as for example cellulose acetate, cellulose nitrate and mixed cellulose ester synthetic membranes.

Suitable glass microfibers include, for example, borosilicate glass, such as the glass fiber filters commercially available from Pall Corporation, USA as Type NE, with a nominal pore size of 1 µm. Illustrative of suitable polymer filters include acrylic co-polymer filters with a pore size 3 µm or less, for example those with pore sizes of 0.2, 0.45, 0.8, 1.2 and 3 µm. Polymer filters of polyamide or of polyvinylchloride with a nominal pore size of 3 µm or less are also widely commercially available. This is also true for cellulose based membranes.

In other embodiments, the filter comprises a metal mesh, for example, of stainless steel, which advantageously has a pore size of less than 3 µm. Other suitable materials include, for example, polymer films provided that they have a suitable level of air permeability.

After use of the dose collection device, the filter F containing the collected particles is subjected to IVRT, and thus needs to be transferred in a corresponding IVRT apparatus, using IVRT devices.

FIGS. 6 to 9 show three embodiments of IVRT devices according to the present invention.

Figure 2:
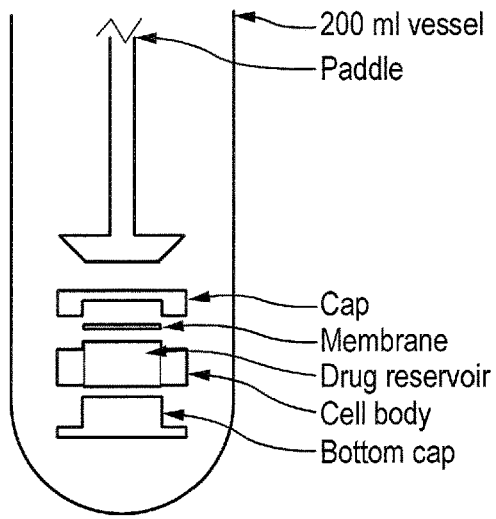
FIG. 2 is a schematic view of an immersion cell type apparatus.
Figure 6:
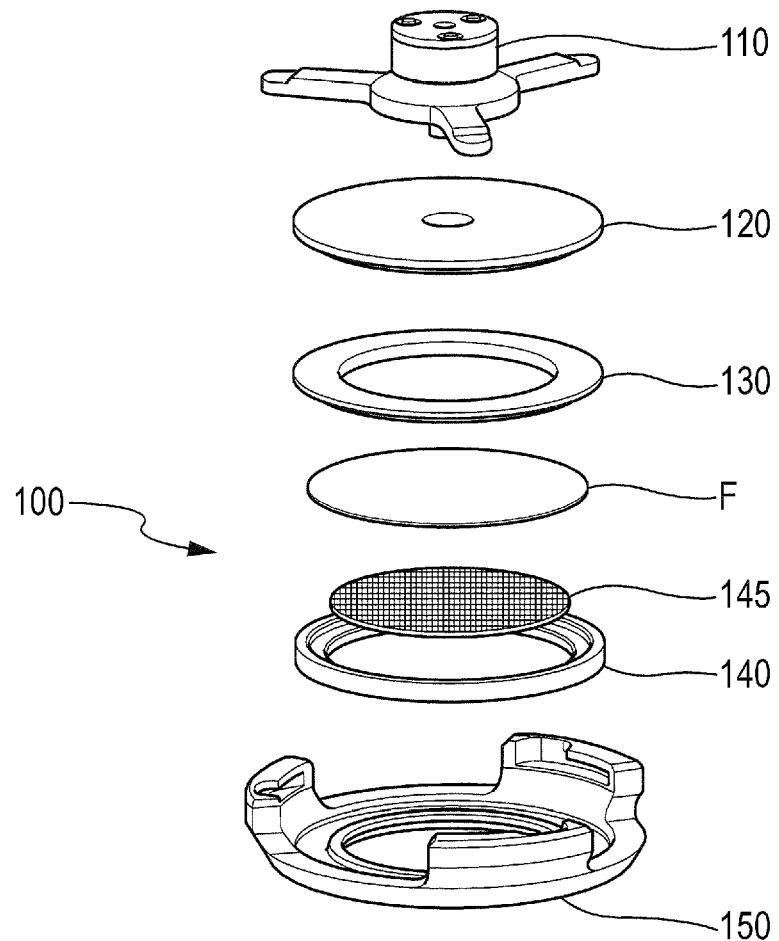
FIG. 6 is a schematic exploded perspective view of an IVRT device according to a first advantageous embodiment of the present invention.
Figure 7:
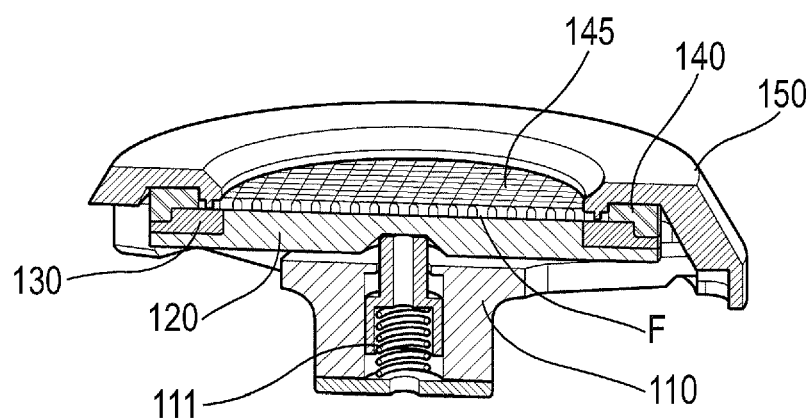
FIG. 7 shows a section through the IVRT device of FIG. 6.

FIGS. 6 and 7 show a first embodiment wherein the IVRT device 100 is adapted for an immersion cell apparatus shown in FIG. 2.

Figure 1:
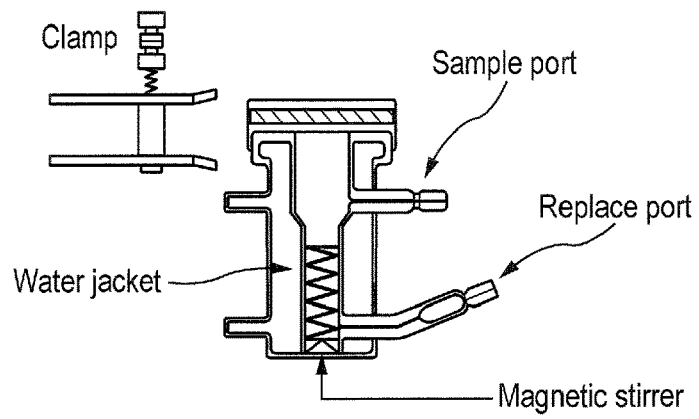
FIG. 1 is a schematic view of a vertical diffusion cell system.
Figure 8:
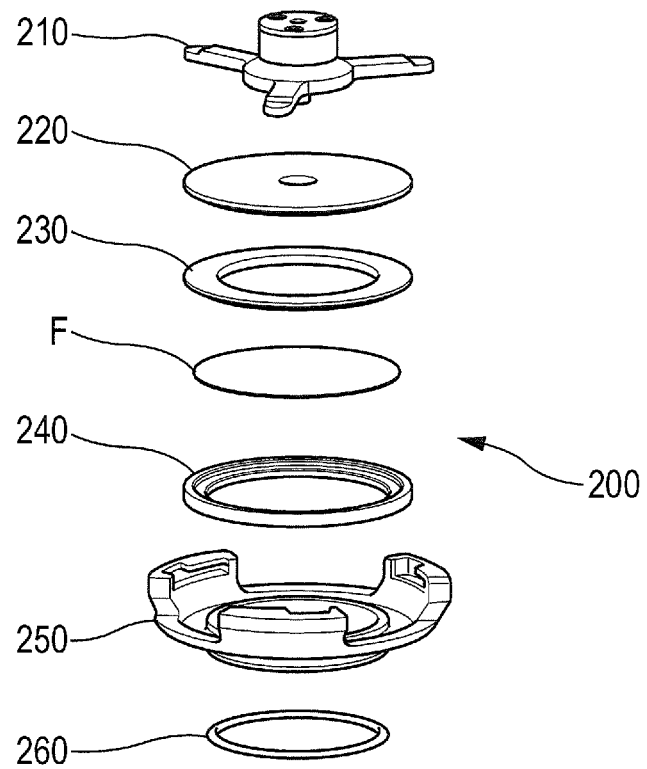
FIG. 8 shows schematic exploded perspective view of an IVRT device according to a second advantageous embodiment of the present invention.

FIG. 8 shows a second embodiment wherein the IVRT device 200 is adapted for a VDC apparatus shown in FIG. 1.

Figure 3:
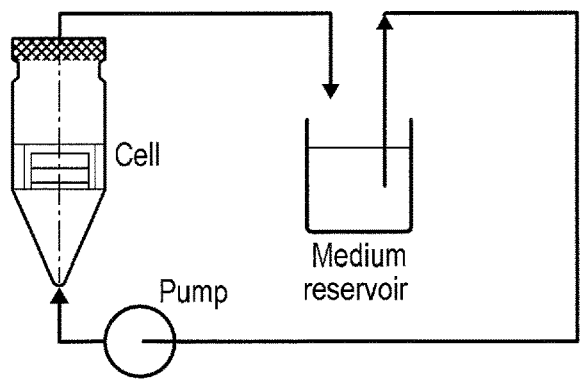
FIG. 3 is a schematic view of a USP 4 flow-through cell apparatus.
Figure 9:
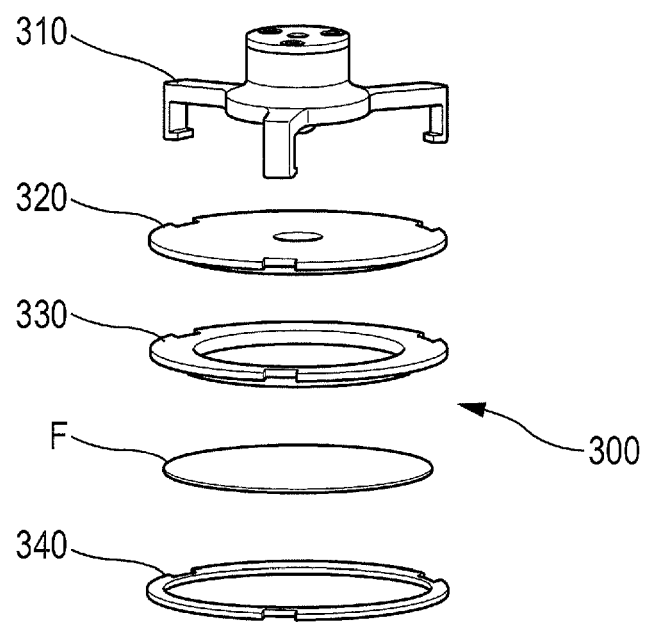
FIG. 9 shows schematic exploded perspective view of an IVRT device according to a third advantageous embodiment of the present invention.

FIG. 9 shows a third embodiment wherein the IVRT device 300 is adapted for a USP 4 flow-through cell apparatus shown in FIG. 3.

The IVRT device 100 according to the first embodiment comprises a filter cover retainer 110, a filter cover 120, an upper filter support element 130, the filter F, a lower filter support element 140, a mesh 145 interposed between the filter F and the lower filter support element 140 and a holder member 150.

The IVRT device 200 according to the second embodiment comprises a filter cover retainer 210, a filter cover 220, an upper filter support element 230, the filter F, a lower filter support element 240, a holder member 250, and an O-ring 260.

The IVRT device 300 according to the third embodiment comprises a filter cover retainer 310, a filter cover 320, an upper filter support element 330, the filter F and a lower filter support element 340.

FIGS. 10 to 18 show the basic steps involved in dose collection for all three IVRT devices, using the dose collection device 10 described above. Upon dose collection, there are different options for sealing the membrane depending on the IVRT device to be used, as will be detailed afterwards.

The steps for handling the filter F as shown in FIGS. 10 to 18 are related to the lower body 50, and said steps are shown from above said lower body. Said steps are identical for all three IVRT devices.

Figure 10:
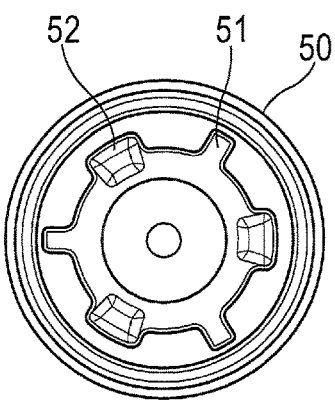
FIGS. 10 to 18 show schematic views of the steps for dose collection.

FIG. 10 shows the lower body 50 seen from above, with the first and second recesses 51, 52.

Figure 11:
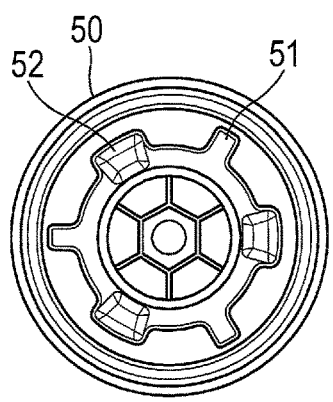

FIG. 11 shows the lower body 50 provided with a filter base, which is either permanently bonded to the lower body 50 or can be fitted and removed from the lower body.

Figure 12:
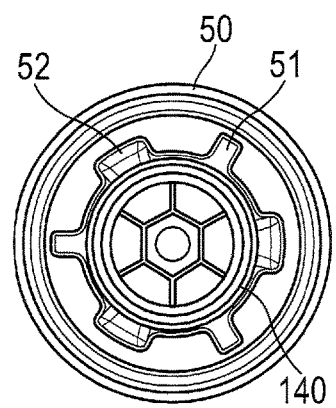

FIG. 12 shows the lower filter support element 140 added on said filter base.

Figure 13:
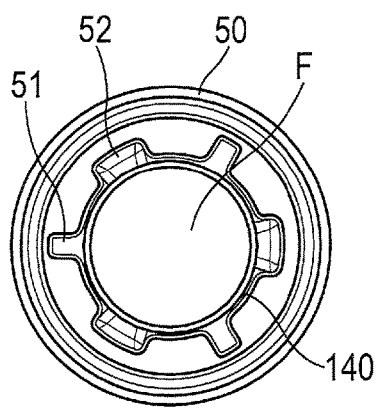

FIG. 13 shows the filter F added onto the lower filter support element.

Figure 14:
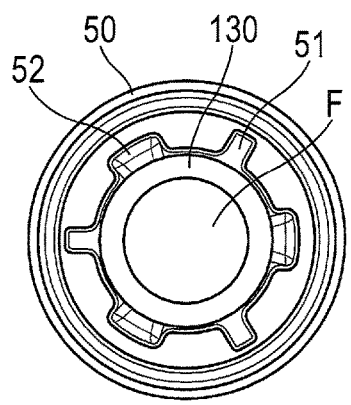

FIG. 14 shows the upper filter support element 130 added onto the filter F.

Figure 15:
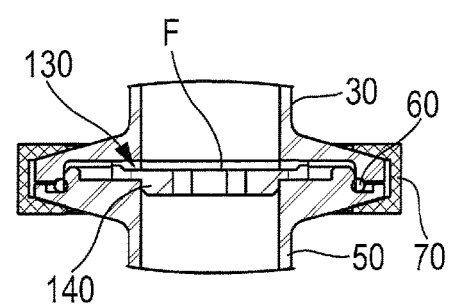

FIG. 15 shows the assembly and clamping of the upper body 30 on the lower body 50, thus compressing the O-ring 70 and maintaining the filter F in its dose collection position. In this position, the dose collection device 10 can be used to collect a dose on the filter F, as described above.

Figure 16:
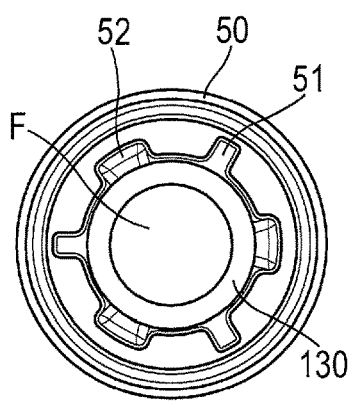

FIG. 16 shows the device after removal of the upper body 30, thus similar as in FIG. 14, but with the filter F loaded with particles.

Figure 17:
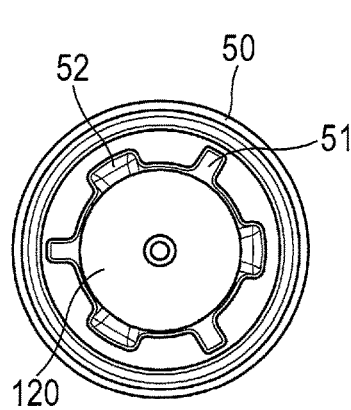

FIG. 17 shows the fitting of the filter cover 120 onto the drug coated filter F to occulate and protect the collected dose.

Figure 18:
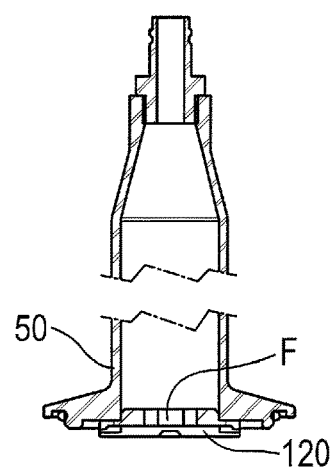

FIG. 18 shows the removal of the lower body 50 and of the filter base, if not bonded into the lower body. This step is done by putting lower body upside down, as shown in FIG. 18.

At this stage, there remains a unit formed by the lower filter support element 140, the loaded filter F, the upper filter support element 130 and the filter cover 120. This unit is then placed in an IVRT device, to be used in a corresponding IVRT apparatus.

Figure 19:
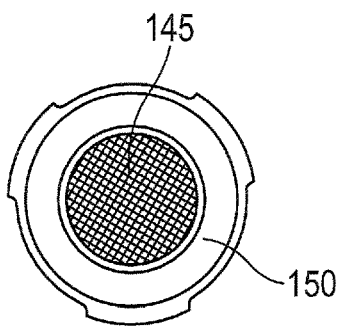
FIGS. 19 to 21 show schematic views of the steps for transferring the loaded filter in an IVRT device as shown in FIGS. 6 and 7.
Figure 20:
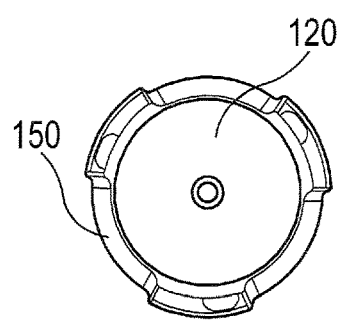
Figure 21:
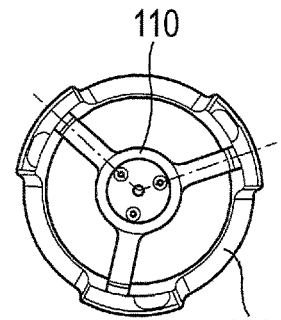

FIGS. 19 to 21 show how the assembly is put together for the immersion cell apparatus shown in FIG. 2. FIG. 19 is seen from below and FIGS. 20 and 21 are seen from above. The unit formed by the lower filter support element 140, the loaded filter F, the upper filter support element 130 and the filter cover 120 is positioned into the holder member 150 with the addition of a suitable mesh 145. The filter cover retainer 110 comprises three legs and has a spring 111 to control the compressive load between the holder member 150, the lower filter support element 140, the filter F, the upper filter support element 130 and the filter cover 120. This filter cover retainer 110 clamps the assembly together and ensures that the drug coated filter F is occluded from the receptor medium in the dissolution vessel and can therefore be fully immersed. The filter cover retainer 110 is fitted on the holder member 150, as seen on FIG. 21, and rotated to seal the assembly by a well-known bayonet fitting.

Figure 22:
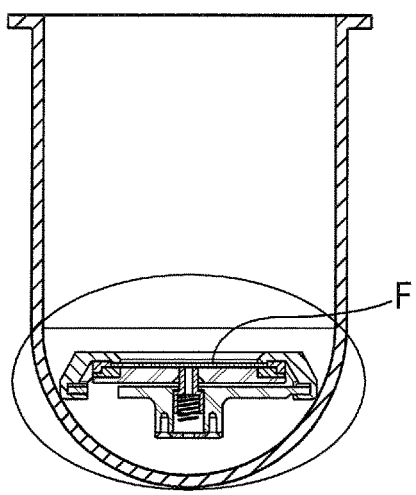
FIGS. 22 and 23 are schematic views of the IVRT device of FIGS. 6 and 7 placed in an immersion cell apparatus as shown in FIG. 2.
Figure 23:
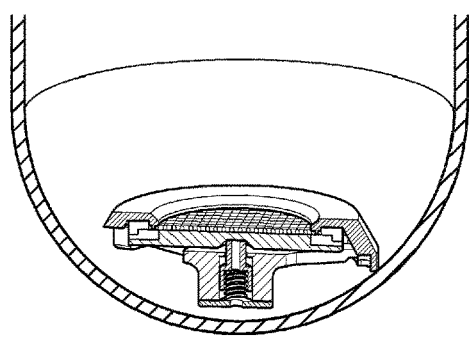

As shown on FIGS. 22 and 23, the assembled cell can then be inserted into a dissolution vessel. The outer dimension and pitch of the holder member 150 is designed to sit in a horizontal position within the glass vessel with respect to the curvature of the vessel. This enables the correct height of the cell within the vessel to be controlled and ensures that the cell surface is aligned with respect to the stirrer paddle of the immersion cell apparatus.

Figure 24:
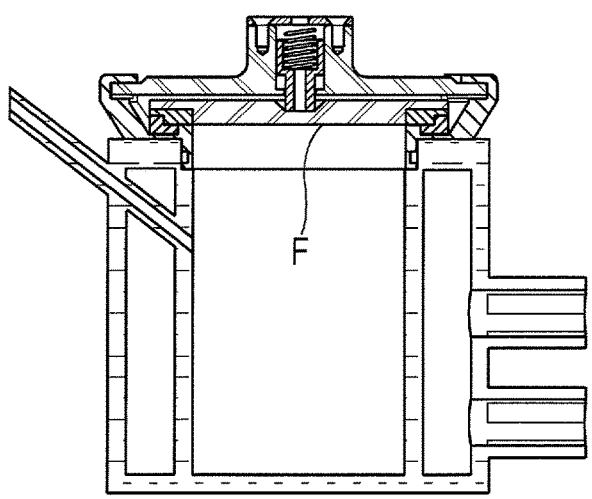
FIG. 24 is a schematic view of the IVRT device of FIG. 8 placed on a VDC apparatus as shown in FIG. 1.

FIG. 24 refers to a VDC apparatus with the IVRT device of FIG. 8. This enables the insertion of the occluded cell directly into contact with a receptor medium within a jacketed vertical diffusion cell as shown in FIG. 24. The diffusive communication between the occluded aerosol dose and the reservoir takes place through contact of the receptor media with the filter. It should be noted that the diameters of the exposed filter, of the donor chamber and of the receptor chamber, which define the dosage delivery surface area for the test, need to be similar and within ±5% of the specified diameter.

Figure 25:
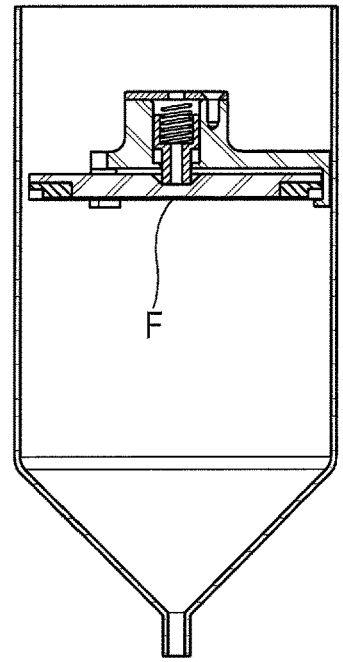
FIG. 25 is a schematic view of the IVRT device of FIG. 9 placed in a USP 4 flow-through cell apparatus as shown in FIG. 3.

FIG. 25 refers to a USP 4 flow-through cell apparatus with the IVRT device of FIG. 9. The holder assembly for a USP 4 flow-through cell is quite different to the other two assemblies described above. It has a different lower filter support element 340 (which has three sections for clamping) in the lower air chamber which enables clamping and occlusion of the aerosol dose without a holder member. The assembled and sealed insertion cell in a USP 4 flow-through cell is shown in FIG. 25. The area for initial alignment of the three-legged clamp, upon sealing and occluding the assembly, enables sufficient a gap for the flow of the receptor media (in either an open or closed system) to make contact with the diffusional area of the exposed filter and exit of the continuous flow through the top of the USP 4 cell.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

The invention claimed is:

1. An in vitro release testing (IVRT) device for orally inhaled drug products, for use in an IVRT apparatus, said device comprising an air-permeable filter loaded with particulate material representing a dose of an orally inhaled drug product, said device comprising:
   an upper filter support element and a lower filter support element, said loaded filter being circumferentially retained between said upper and lower support elements,
   a filter cover to cover the upper surface of said loaded filter, and
   a filter cover retainer provided to assemble and seal the IVRT device, said filter cover retainer having a spring to control the compressive load between said lower filter support element, said filter, said upper filter support element and said filter cover.

2. A device according to claim 1, further comprising a holder member receiving said lower filter support element and cooperating with said filter cover retainer for the sealed assembly of the IVRT device.

3. A device according to claim 2, wherein said filter cover retainer comprises legs providing a bayonet-type fitting on said holder member.

4. A device according to claim 2, wherein said filter cover retainer comprises three legs providing a bayonet-type fitting on said holder member.

5. A device according to claim 2, wherein a mesh is provided between said lower filter support element and said loaded filter to cover the lower surface of said loaded filter.

6. A device according to claim 1, wherein said filter cover retainer cooperates directly with said lower filter support element for the sealed assembly of the IVRT device.

7. A device according to claim 1, wherein said filter is selected from woven fabrics, nonwoven fabrics, meshes and air-permeable films.

8. A device according to claim 7, wherein the filter comprises a fabric formed from glass microfibers, synthetic cellulose based materials, or from filaments of a polymeric material selected from polycarbonate, polyester, polyolefins, polyamides, polyvinylchlorides and polyetheretherketones.

9. A device according to claim 7, wherein the filter comprises a metal mesh.

10. A device according to claim 7, wherein the filter comprises a stainless steel metal mesh.

11. A device according to claim 1, wherein said filter has a pore size of not more than 5 μm.

12. A device according to claim 1, wherein said filter has a pore size of at least 1 μm.

13. A device according to claim 1, wherein said filter has an air permeability which is such that the filter generates a reduction in flow rate of not more than 20% relative to absence of a filter.

14. A device according to claim 1, wherein said filter has a pore size of not more than 3 μm.

15. A device according to claim 1, wherein said filter has an air permeability which is such that the filter generates a reduction in flow rate of not more than 15% relative to absence of a filter.

16. A device according to claim 1, wherein said filter has an air permeability which is such that the filter generates a reduction in flow rate of not more than 10% relative to absence of a filter.

* * * * *